United States Patent [19]

Yokoyama et al.

[11] 4,400,199
[45] Aug. 23, 1983

[54] THIOLCARBAMATE COMPOUNDS AND THEIR USE AS HERBICIDES

[75] Inventors: Shigeo Yokoyama; Teruyuki Misumi; Einosuke Fujimoto; Yutaka Kobayashi, all of Yokohama, Japan

[73] Assignee: Asahi Kasei Kabashiki Kaisha, Tokyo, Japan

[21] Appl. No.: 316,305

[22] Filed: Oct. 29, 1981

[51] Int. Cl.³ .................. A01N 47/16; C07D 211/16
[52] U.S. Cl. .......................................... 71/88; 71/94; 260/239 BF; 546/245
[58] Field of Search ................. 260/239 BF; 546/245; 71/88, 94

[56] References Cited

U.S. PATENT DOCUMENTS 3,066,020  11/1962  Tilles et al. ................... 546/245
3,708,471  1/1973   Rohr et al. ................... 260/239 BF
4,299,765  11/1981  Tilles ............................. 71/88

FOREIGN PATENT DOCUMENTS 2333397  1/1975  Fed. Rep. of Germany .... 260/239 BE

OTHER PUBLICATIONS

Tilles, Chem. Abstracts, vol. 73, Abstract No. 55977m (1970).

Primary Examiner—Alton D. Rollins
Attorney, Agent, or Firm—Wyatt, Gerber, Shoup, Scobey & Badie

[57] ABSTRACT

Chloroalkylthiolcarbamate compounds of the formula:

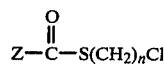

wherein Z represents

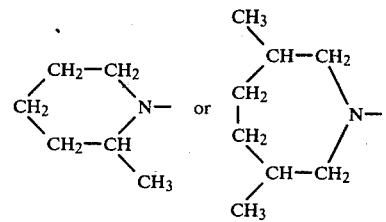

and when Z is

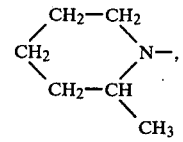

n is an integer of 4 to 10, whereas when Z is

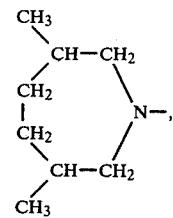

n is an integer of 3 to 10. These compounds are useful as effective herbicides having no harmful effect on the ecosystem, particularly extremely low toxicity to fish, and can be obtained, for example, by reacting the corresponding thiolcarbamate derivatives with a chloroalkyl halide.

10 Claims, No Drawings

THIOLCARBAMATE COMPOUNDS AND THEIR USE AS HERBICIDES

This invention relates to a new class of chloroalkyl-thiolcarbamate compounds and their use as herbicides.

More particularly it is concerned with a chloroalkyl-thiolcarbamate compound represented by the formula (I):

wherein Z represents

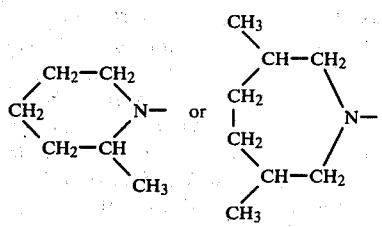

and when Z is

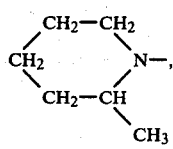

n is an integer of 4 to 10, whereas when Z is

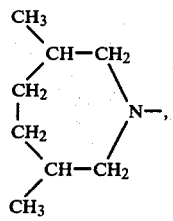

n is an integer of 3 to 10, a herbicidal composition which comprises as an active ingredient the compound (I) and an agriculturally acceptable carrier, and a method for the destruction of undesirable weeds which comprises applying to said weeds a herbicidal amount of the compound (I). The new compound (I) has very effective herbicidal activity with extremely low toxicity, either acute or subacute, to fish.

In the recent years, a number of herbicides have been developed and put on the market, greatly contributing to a farm labor saving and an increase in crop production. They are usually assured of their reliable safety to warm-blooded animals (homoiothermic animals). They do, however, often unexpectedly exert a toxic action to creatures living in and around a paddy field, especially to those living in the hydrosphere, even when they are used under multiple restrictions regarding the timing of application, the quantity, the variety of crop and other factors. In fact, it has been reported that some types of herbicides have accidentally killed culture carps.

When thiolcarbamate type herbicides are used, it is recommended that they be applied in conformity with the minutely prescribed precautions, and that a closing barrier be installed in the paddy field to which the herbicide has been applied so that the water in the paddy field may be prevented from flowing out to the surrounding hydrosphere for a predetermined period of time. These efforts have been successful to a certain extent.

However, it is needless to say that it is the most desirable to develop a herbicide having excellent herbicidal activity but no secondarily occurring harmful effect on creatures living in the hydrosphere. From this viewpoint, a number of researches have been made to develop agricultural chemicals with decreased acute toxicity to fish.

Hitherto, various researches have been made to develop and use thiolcarbamate compounds having a herbicidal activity. For example, it was suggested in Japanese Patent Application Publication No. 12119/1966 to use as a herbicide a thiolcarbamate derivative represented by the formula (II):

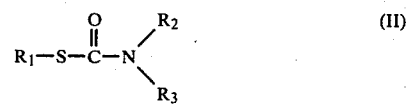

wherein $R_1$ represents a methylmercaptomethyl group, a lower chloroalkyl group, a 3-chloro-2-butenyl group, a propargyl group or a group of the formula

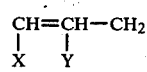

in which X and Y represent a bromine atom and a hydrogen atom, respectively, or vice versa, and $R_2$ and $R_3$ each independently represent an alkyl group, an alkenyl group, a cycloalkyl group or a chloroalkenyl group, or $R_2$ and $R_3$ represent groups which cooperate with each other to form a piperidino ring or alkyl-substituted piperidino ring together with the nitrogen atom. In the above formula (II), $R_2$ and $R_3$ each independently may represent an alkynyl group when $R_1$ is a lower chloroalkyl group, and $R_1$ and $R_2$ each independently may represent a lower alkyl group, a lower alkenyl group, a methoxyalkyl group or a haloalkenyl group when $R_3$ is a methallyl group.

It was also suggested in U.S. Pat. No. 3,066,020 to use as a herbicide a thiolcarbamate derivative represented by the formula (III):

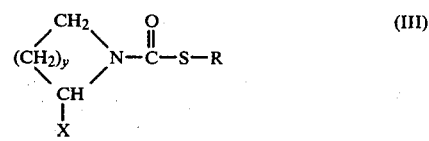

wherein R represents a lower alkyl group, either straight or branched chain, a lower alkenyl group, a lower alkynyl group, a lower chloroalkyl group, a lower chloroalkenyl group or a methoxy lower alkyl group, X represents a hydrogen atom or a lower alkyl group and y is an integer of 2 to 3.

It was further suggested in Japanese Patent Application Laid-Open Specification No. 36632/1975 to use as a herbicide a thiolcarbamate derivative represented by the formula (IV):

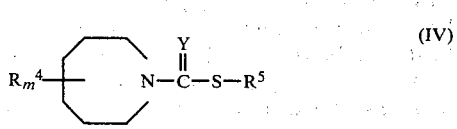

wherein Y represents an oxygen atom or a sulfur atom, $R^4$ represents a methyl group or an ethyl group, m is an integer of 2 to 3, but m may be 1 when $R^4$ is an ethyl group, and $R^5$ represents an aliphatic group substituted with one or more halogen atoms, hydroxyl radicals, cyano radicals or alkoxy radicals or a group of the formula:

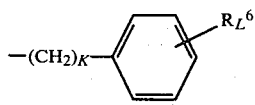

in which $R^6$ represents a halogen atoms, a nitro radical, a cyano radical, a methoxy radical, an ethoxy radical or an alkyl radical, K is an integer of 0 to 2, and L is an integer of 0 to 4.

In the just above formula, $R^6$'s may be the same or different when L is 2 or greater.

In Japan, however, none of these thiolcarbamate compounds disclosed in the above patent application specifications has been put to practical use as herbicides.

To our knowledge, as examples of the herbicides with a thiolcarbamate structure commercially available and put to practical use in Japan, there can be mentioned S-p-chlorobenzyl-N,N-diethyl-thiolcarbamate of the formula:

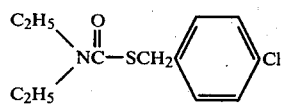

according to Japanese Patent Application Publication No. 29024/1968 (available under common name "Benthiocarb" or "Thiobencarb"), and S-ethyl-hexahydro-1H-azapine-1-carbothioate of the formula:

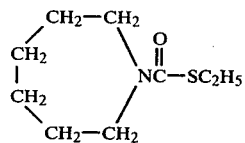

according to Japanese Patent Publication No. 1699/1964 (available under common name "Molinate"). Especially, the latter compound has enjoyed good reputation for its excellent activity to combat barnyard grasss, so that it is regarded as one of the essential chemicals for growing rice plants.

However, there is a continuous demand in the art for much more effective herbicidal compounds which will not impose harmful effect on the ecosystem, particularly to creatures living in the hydrosphere on and around a paddy field.

We have made intensive studies on thiolcarbamate moiety-containing substances, including S-ethyl-hexahydro-1H-azepine-1-carbothioate (Molinate) known to be effective to combat barnyard grass, their herbicidal activities, and acute and subacute toxicity to fish.

As a result, we have found that the thiolcarbamate compounds having the above mentioned formula (I) show prominent herbicidal activities, especially against barnyard grass, a predominant weed on paddy field, up to its 3 leaf-stage or so, and that it has no harmful effect on rice plants and ensures safety to fish. Namely, its acute toxicity to fish is extremely low and it does not cause subacute anemia symptoms in fish as experienced with the conventional thiolcarbamate herbicides, such as Molinate.

The compounds employed in our tests as to effectiveness against weeds, phytotoxicity to rice plants and acute or subacute toxicity to fish included the thiolcarbamate compounds of the formulae (II), (III) and (IV) structurally similar to that of the formula (I). The comparative test results are shown in Experiments which will be given later. As a result of the test, it has been revealed that the compound of the formula (I) is extremely effective for destroying weeds, does not have phytotoxicity to rice plants and ensures safety to fish, and that the other compounds tested have a drawback in one point or another.

It is, therefore, an object of the present invention to provide a new class of chloroalkylthiolcarbamate compounds which have prominent herbicidal activities to destroy unfavorable weeds such as barnyard grass or the like and which however will not have any toxicity, either acute or subacute, to fish and other creatures living in the hydrosphere.

It is another object of the present invention to provide an effective herbicidal composition containing such a compound of the kind described above.

The foregoing and other objects, features and advantages of the present invention will be apparent to those skilled in the art from the following detailed description and appended claims.

In one aspect of this invention, there is provided a new class of chloroalkylthiolcarbamate compounds represented by the formula (I):

wherein Z represents

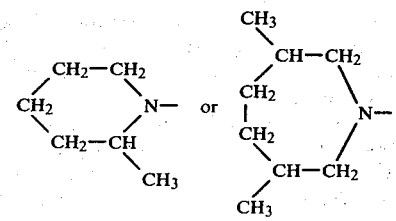

and when Z is

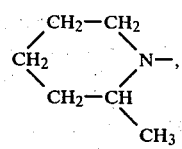

n is an integer of 4 to 10, whereas when Z is

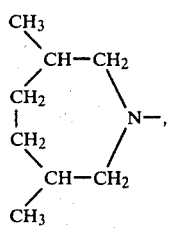

n is an integer of 3 to 10. If n is greater than 10 in the above formula (I), it was found that the effectiveness against weeds would drastically decrease.

In particular, the following compounds of the general formula (I) according to the present invention are preferable from the viewpoints of performance superiority over the conventional chemicals as is clear from Experiments, which will be given later, raw material availability and costs:

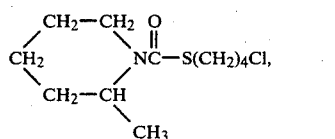

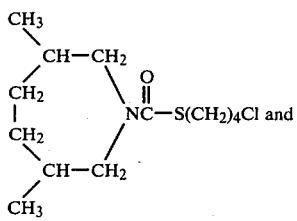

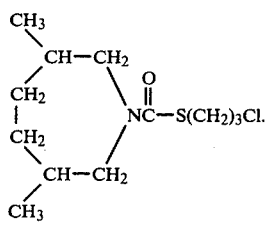

In another aspect of the present invention, there is provided a herbicidal composition which comprises as an active ingredient the compound (I) and an agriculturally acceptable carrier.

In a further aspect of the present invention, there is provided a method for the destruction of undesirable weeds which comprises applying to said weeds a herbicidal amount of the compound (I).

The present compounds (I) are new substances not disclosed in literature and can be easily prepared, for example, by conducting a substitution reaction as shown in the following chemical equation:

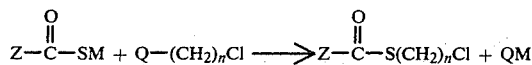

In the above chemical equation, Z and n are as defined above, M stands for an alkali metal ion, such as sodium ion or potassium ion, a tertiary amine ammonium ion, such as triethyl ammonium ion, or $(ZH_2)^+$, and Q stands for a halogen atom, preferably a bromine or iodine atom, still satisfactorily a chlorine atom.

In conducting the above substitution reaction, the molar ratio of $Q-(CH_2)_nCl$ to

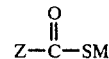

may be 1.0 to 2.0. The above-mentioned reaction may be effected in the presence or absence of a solvent. As the solvent suitable for the reaction, there may be mentioned a low-polarity organic solvent, such as benzene, toluene, ether, chloroform, or the like, and a high-polarity organic solvent, such as N,N-dimethylformamide, N-methyl-2-pyrrolidone, or the like. This reaction may be effected at a temperature of room temperature of 100° C., more preferably 40° to 80° C. under the atmospheric pressure.

Preparation of the compounds of the general formula (I) is illustrated hereinbelow by the following Examples.

EXAMPLE 1

S-(4-chlorobutyl)-(2-methyl)-piperidine-1-carbothioate

Compound 1

In a 1-liter four necked flask equipped with a stirrer and a reflux condenser were charged 52 g (0.2 mol) of triethylammonium-(2-methyl)-piperidine-1-carbothioate and 250 g of toluene. 51 g (0.30 mol) of 1-bromo-4-chlorobutane was weighed and put into a 200 ml dropping funnel. The dropping funnel was attached to the above-mentioned flask. The flask was put in a water bath, stirring was begun and 1-bromo-4-chlorobutane in the dropping funnel was dropwise added to the solution in the flask while controlling the dropping rate so that the solution temperature in the flask is kept at about 45° C. After completion of the dropwise addition, the reaction was continued for further 10 hours while controlling the water-bath temperature at 45° C.

After completion of the reaction, the reaction mixture was transferred into a 1-liter separatory funnel and washed with 300 ml of a 0.2 N aqueous NaOH solution two times and then washed with 300 ml of a 0.2 N aqueous HCl solution two times. Further, the reaction mixture was repeatedly washed with water until the water layer became substantially neutral. The obtained organic layer was withdrawn from the separatory funnel and dried over anhydrous sodium sulfate, followed by filtration. The organic layer thus obtained was charged into a rotary evaporator and toluene was removed at 50° C. under a pressure of 10 mmHg. The residue was put in a vacuum dryer and allowed to stand overnight at 50° C. under a pressure of 1 mmHg to remove low boiling point components.

Thus, there was obtained 43 g of a crude product. The crude product was quantitatively analyzed by means of gas chromatography. The yield of S-(4-chlorobutyl)-(2-methyl)-piperidine-1-carbothioate based on the triethyl-ammonium-(2-methyl)-piperidine-1-carbothioate was 77%.

10 g of the crude product was subjected to purification by means of Prep LC/System 500 Liquid Chromatograph (manufactured and solid by Waters Assoc. Inc., U.S.A.). A mixed solution of 99 volume % of n-hexane and 1 volume % of acetone was employed as the solvent, and passed through Porasil Column (manufactured and sold by Waters Assoc. Inc., U.S.A.). The fraction was concentrated by means of a rotary evaporator and then dried overnight at 50° C. under a pressure of 1 mmHg. There was obtained 8 g of the intended product (Compound 1), S-(4-chlorobutyl)-(2-methyl)-piperidine-1-carbothioate represented by the formula

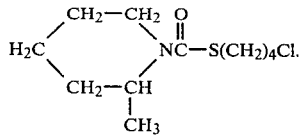

The refractive index $n_D^{25}$ of the compound was 1.5198.

EXAMPLE 2

S-(5-chloropentyl)-(2-methyl)-piperidine-1-carbothioate

Compound 2

Substantially the same procedures as in Example 1 were repeated except that 56 g (0.30 mol) of 1-bromo-5-chloropentane was used instead of 1-bromo-4-chlorobutane. There was obtained 45 g of a crude product. The yield of S-(5-chloropentyl)-(2-methyl)-piperidine-1-carbothioate based on the triethylammonium-(2-methyl)-piperidine-1-carbothioate was 78%. Using 10 g of the crude product, substantially the same procedures as in Example 1 were repeated to obtain 6 g of the intended product (Compound 2), S-(5-chloropentyl)-(2-methyl)-piperidine-1-carbothioate represented by the formula

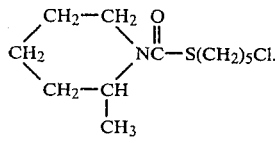

The refractive index $n_D^{25}$ of the compound was 1.5191.

EXAMPLE 3

S-(6-chlorohexyl)-(2-methyl)-piperidine-1-carbothioate

Compound 3

Substantially the same procedures as in Example 1 were repeated except that 60 g (0.30 mol) of 1-bromo-6-chlorohexane was used instead of 1-bromo-4-chlorobutane. There was obtained 47 g of a crude product. The yield of S-(6-chlorohexyl)-(2-methyl)-piperidine-1-carbothioate based on the triethylammonium-(2-methyl)-piperidine-1-carbothioate was 77%. Using 10 g of the crude product, substantially the same procedures as in Example 1 were repeated to obtain 7 g of the intended product (Compound 3), S-(6-chlorohexyl)-(2-methyl)-piperidine-1-carbothioate represented by the formula

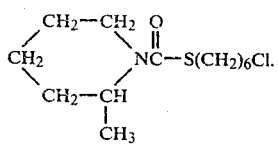

The refractive index $n_D^{25}$ of the compound was 1.5141.

EXAMPLE 4

S-(8-chlorooctyl)-(2-methyl)-piperidine-1-carbothioate

Compound 4

Substantially the same procedures as in Example 1 were repeated except that 68 g (0.30 mol) of 1-bromo-8-chlorooctane was used instead of 1-bromo-4-chlorobutane. There was obtained 48 g of a crude product. The yield of S-(8-chlorooctyl)-(2-methyl)-piperidine-1-carbothioate based on the triethylammonium-(2-methyl)-piperidine-1-carbothioate was 70%. Using 10 g of the crude product, substantially the same procedures as in Example 1 were repreated to obtain 8 g of the intended product (Compound 4), S-(8-chlorooctyl)-(2-methyl)-piperidine-1-carbothioate represented by the formula

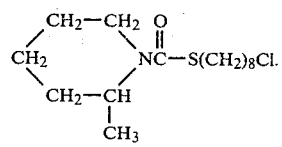

The refractive index $n_D^{25}$ of the compound was 1.5087.

EXAMPLE 5

S-(10-chlorodecyl)-(2-methyl)-piperidine-1-carbothioate

Compound 5

Substantially the same procedures as in Example 1 were repeated except that 77 g (0.30 mol) of 1-bromo-10-chlorodecane was used instead of 1-bromo-4-chlorobutane. There was obtained 45 g of a crude product. The yield of S-(10-chlorodecyl)-(2-methyl)-piperidine-1-carbothioate based on the triethylammonium-(2-methyl)-piperidine-1-carbothioate was 60%. Using 10 g of the crude product, substantially the same procedures as in Example 1 were repeated to obtain 8 g of the intended product (Compound 5), S-(10-chlorodecyl)-(2-methyl)-piperidine-1-carbothioate represented by the formula

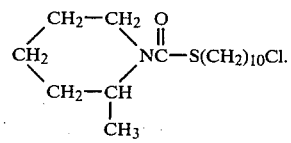

The refractive index $n_D^{25}$ of the compound was 1.5068.

EXAMPLE 6

S-(3-chloropropyl)-3,6-dimethyl-hexahydro-1H-azepine-1-carbothioate

Compound 6

In a 1-liter four necked flask equipped with a stirrer and a reflux condenser were charged 58 g (0.2 mol) of triethylammonium-3,6-dimethyl-hexahydro-1H-azepine-1-carbothioate and 250 g of toluene. 47 g (0.30 mol) of 1-bromo-3-chloropropane was weighed and put into a 200 ml dropping funnel. The dropping funnel was attached to the above-mentioned flask. The flask was put in a water bath, stirring was begun and 1-bromo-3-chloropropane in the dropping funnel was dropwise added to the solution in the flask while controlling the dropping rate so that the solution temperature in the flask is kept at about 50° C. After completion of the dropwise addition, the reaction was continued from further 12 hours while controlling the water-bath temperature at 50° C.

Substantially the same procedures as in Example 1 were repeated to obtain 44 g of a crude product. Quantitative analysis of the thus obtained crude product by means of gaschromatography showed that the yield of S-(3-chloropropyl)-3,6-dimethyl-hexahydro-1H-azepine-1-carbothioate based on the triethylammonium-3,6-dimethyl-hexahydro-1H-azepine-1-carbothioate was 72%. Using 10 g of the crude product, substantially the same procedures as in Example 1 were repeated to obtain 7 g of the desired product (Compound 6), S-(3-chloropropyl)-3,6-dimethyl-hexahydro-1H-azepine-1-carbothioate represented by the formula

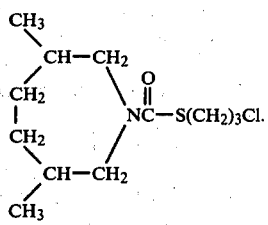

The refractive index $n_D^{25}$ of the compound was 1.5160.

EXAMPLE 7

S-(4-chlorobutyl)-3,6-dimethyl-hexahydro-1H-azepine-1-carbothioate

Compound 7

Substantially the same procedures as in Example 6 were repeated except that 51 g (0.30 mol) of 1-bromo-4-chlorobutane was used instead of 1-bromo-3-chloropropane. There was obtained 50 g of a crude product. The yield of S-(4-chlorobutyl)-3,6-dimethyl-hexahydro-1H-azepine-1-carbothioate based on the triethylammonium-3,6-dimethyl-hexahydro-1H-azepine-1-carbothioate was 78%. Using 10 g of the crude product, substantially the same procedures as in Example 1 were repeated to obtain 8 g of the intended product (Compound 7), S-(4-chlorobutyl)-3,6-dimethyl-hexahydro-1H-azepine-1-carbothioate represented by the formula

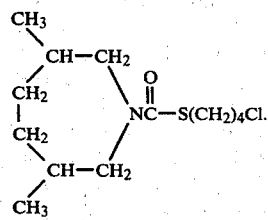

The refractive index $n_D^{25}$ of the compound was 1.5152.

EXAMPLE 8

S-(6-chlorohexyl)-3,6-dimethyl-hexahydro-1H-azepine-1-carbothioate

Compound 8

Substantially the same procedures as in Example 6 were repeated except that 56 g (0.30 mol) of 1-bromo-6-chlorohexane was used instead of 1-bromo-3-chloropropane. There was obtained 55 g of a crude product. The yield of S-(6-chlorohexyl)-3,6-dimethyl-hexahydro-1H-azepine-1-carbothioate based on the triethylammonium-3,6-dimethyl-hexahydro-1H-azepine-1-carbothioate was 78%. Using 10 g of the crude product, substantially the same procedures as in Example 1 were repeated to obtain 7 g of the intended product (Compound 8), S-(6-chlorohexyl)-3,6-dimethyl-hexahydro-1H-azepine-1-carbothioate represented by the formula

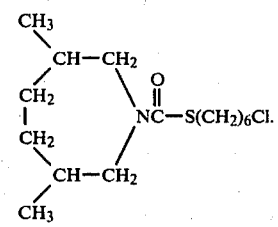

The refractive index $n_D^{25}$ of the compound was 1.5095.

EXAMPLE 9

S-(10-chlorodecyl)-3,6-dimethyl-hexahydro-1H-azepine-1-carbothioate

Compound 9

Substantially the same procedures as in Example 6 were repeated except that 77 g (0.30 mol) of 1-bromo-10-chlorodecane was used instead of 1-bromo-3-chloropropane. There was obtained 52 g of a crude product. The yield of S-(10-chlorodecyl)-3,6-dimethyl-hexahydro-1H-azepine-1-carbothioate based on the triethylammonium-3,6-dimethyl-hexahydro-1H-azepine-1-carbothioate was 62%. Using 10 g of the crude product, substantially the same procedures as in Example 1 were repeated to obtain 8 g of the intended product (Compound 9), S-(10-chlorodecyl)-3,6-dimethyl-hexahydro-1H-azepine-1-carbothioate represented by the formula

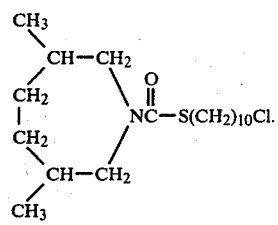

The refractive index $n_D^{25}$ of the compound was 1.5030.

The compounds in this invention may be formulated for use to the preparations commonly employed as a herbicide, for example, powdery dusts, coarse dusts, fine granules, granules, wettabble powders, emulsifiable concentrates, aqueous liquids, water soluble powders, oil suspensions and so on, with admixture of a carrier and, if required, other auxiliary agents. The carrier as used herein means a synthetic or natural and inorganic or organic substance that is mixed with an active compound and can assist an active compound in its arrival to the portion to be treated and make it easy to store, transport or handle.

As suitable solid carriers may be mentioned inorganic substances such as clays, which may be represented by Kaolinite, Montmorillonite or Attapulgite, talc, mica, pyrophyllite, pumice, vermiculite, gypsum, calcium carbonate, dolomite, diatomaceous earth, magnesium carbonate, apatite, zeolite, silicic anhydride, synthetic calcium silicate and the like, vegetable organic substances such as soybean meal, tobacco powder, walnut powder, wheat flour, wood meal, starch, crystalline cellulose and the like, synthetic or natural high polymer compounds such as cumarone resin, petroleum resin, alkyd resin, polyvinyl chloride, polyalkylene glycol, ketone resin, ester gum, copal gum, dammar gum, and the like, waxes such as carnauba wax, beeswax and the like or urea.

As suitable liquid media or carriers may be mentioned paraffin or naphthene hydrocarbons such as kerosene, mineral oil, spindle oil, white oil and the like, aromatic hydrocarbons such as benzene, toluene, xylene, ethylbenzene, cumene, methylnaphthalene and the like, chlorinated hydrocarbons such as carbon tetrachloride, chloroform, trichloroethylene, monochlorobenzene, o-chlorotoluene and the like, ethers such as dioxane, tetrahydrofuran and the like, ketones such as acetone, methylethylketone, diisobutylketone, cyclohexanone, acetophenone, isophorone and the like, esters such as ethyl acetate, amyl acetate, ethylene glycol acetate, diethylene glycol acetate, dibutyl maleate, diethyl succinate and the like, alcohols such as methanol, n-hexanol, ethylene glycol, diethylene glycol, cyclohexanol, benzylalcohol and the like, ether alcohols such as ethylene glycol ethyl ether, ethylene glycol phenyl ether, diethylene glycol ethyl ether, diethylene glycol butyl ether and the like, polar solvents such as dimethylformamide, dimethylsulfoxide and the like or water.

As the surface active agents used for emulsifying, dispersing, wetting, spreading, binding, controlling disintegration, stabilizing active ingredient, improving fluidity, rust proofing and so on may be utilized any of non-ionic, anionic, cationic and amphoteric ones. As suitable non-ionic surface active agents may be mentioned, for example, polymerization adducts of ethylene oxide to higher alcohols such as lauryl alcohol, stearyl alcohol, oleyl alcohol and the like, polymerization adducts of ethylene oxide to alkyl phenols such as isooctyl phenol, nonyl phenol and the like, polymerization adducts of ethylene oxide to alkyl naphthols such as butyl naphthol, octyl naphthol and the like, polymerization adducts of ethylene oxide to higher fatty acids such as palmitic acid, stearic acid, oleic acid and the like, polymerization adducts of ethylene oxide to mono- or dialkyl phosphoric acids such as stearyl phosphoric acid, dilauryl phosphoric acid and the like, polymerization adducts of ethylene oxide to amines such as dodecyl amine, stearic acid amide and the like, polymerization adducts of ethylene oxide to higher fatty acid esters of polyhydric alcohols such as sorbitan and said fatty acid esters, polymerization adducts of ethylene oxide to propylene oxide and so on. As suitable anionic surface active agents may be mentioned, for example, alkyl sulfate salts such as sodium lauryl sulfate, oleyl sulfate amine salt and the like, alkyl sulfonate salts such as sodium dioctyl sulfosuccinate, sodium 2-ethylhexene sulfonate and the like, aryl sulfonate salts such as sodium isopropylnapthalene sulfonate, sodium methylenebisnaphthalene sulfonate, sodium ligninsulfonate, sodium dodecylbenzene sulfonate and the like.

Moreover, the herbicidal compositions of this invention may be used in combination with high molecular compounds or other auxiliary agents such as casein, gelatin, albumin, glue, sodium alginate, carboxymethyl cellulose, methyl cellulose, hydroxyethyl cellulose, polyvinyl alcohol and the like for improving properties and increasing biological effects thereof.

The above-mentioned carriers and various auxiliary agents may be optionally utilized alone or in combination therewith for desired purposes, with consideration for the type of a preparation, application and other factors.

In general, the herbicidal composition of this invention may contain the active compound (I) in an amount of 0.1–99% by weight, based upon the composition.

Dusts usually contain, for example, 1 to 25% by weight of the active compound and the remainder is a solid carrier.

Wettable powders usually contain, for example, 25–90% by weight of the active compound and the remainder is a solid carrier and a dispersing and wetting agent, if required, together with a protective colloidal agent, a thixotropic agent, an anti-foaming agent and the like.

Granules usually contain 1–35% by weight of the active compound and a major portion of the remainder is a solid carrier. The active compound is homogeneously admixed with the solid carrier or adhered or adsorbed on the carrier surface and the size of a granule is about 0.2–1.5 mm.

Emulsifiable concentrates usually contain, for example, 5–50% by weight of the active compound and about 5–20% by weight of an emulsifying agent, the remainder being a liquid carrier, if required, together with a corrosive inhibitor.

The herbicidal compositions of this invention, which are formulated into various types of preparations as mentioned above, may be applied in a paddy field at about 10 to 1,000 g, preferably 60 to 720 g of the active ingredient per 10 ares. When the preparations are applied in too small an amount of the active ingredient, herbicidal effects cannot be obtained. When the preparations are applied in an amount of more than 1 kg/10a. of the active ingredient, unfavorable harmful effects are exerted against crops, and such application is also unfavorable from the standpoint of economy.

The herbicidal compositions of this invention may be preferably combined with other herbicidal active ingredients for broader herbicidal spectra and, in some cases, a synergistic effect is expectable. As examples of such other herbicidal active ingredients may be mentioned, for instance, ethyl 2-methyl-4-chlorophenoxyacetate, ethyl 2-methyl-4-chlorophenoxybutyrate, 2,4,6-trichlorophenyl-4'-nitrophenyl ether, 2,4-dichlorophenyl-3'-methoxy-4'-nitropheyl ether, 2-chloro-2',6'-diethyl-N-(butoxymethyl)acetanilide, methyl-N-(3,4-dichlorophenyl)carbamate, 3,3'-dimethyl-4-methoxybenzophenone, 2-methylthio-4,6-bis(ethylamino)-1,3,5-triazine, S-(2-methyl-1,1-piperidylcarbonylmethyl)O,O-di-n-propyldithiophosphate, O,O-diisopropyl-S-[2-(benzenesulfonamide)ethyl]dithiophosphate, 3-isopropyl-2,1,3-benzothiadiazinone(4)-2,2-dioxide, 3,4-dichloropropionanilide and the like.

Examples of the preparations of the present herbicidal composition are given below, but they are not intended to limit the scope of this invention. All parts are given by weight hereinafter unless otherwise specified.

EXAMPLE 10

Emulsifiable concentrates

50 Parts of Compound 1 prepared according to Example 1 of the present invention, 35 parts of xylene and 15 parts of "Sorpol" (trade name of a surface active agent available from Toho Chemical Industry Company, Japan) were blended and homogeneously dissolved to form emulsifiable concentrates.

EXAMPLE 11

Granules

8 Parts of Compound 2 prepared according to Example 2 of the present invention, 15 parts of bentonite, 44.5 parts of talc, 30 parts of clay, 2 parts of sodium lignosulfonate, 0.5 part of sodium dodecylbenzenesulfonate and 25 parts of water were mixed and then pulverized. The pulverized mixture was molded into cylindrical granules having a diameter of 0.8 mm and a length of 1 to 2 mm, followed by drying.

EXAMPLE 12

Powdery dusts

7 Parts of Compound 3 prepared according to Example 3 of the present invention, 44.5 parts of talc, 45 parts of clay, 3 parts of white carbon and 0.5 part of sodium dodecylbenzenesulfonate were mixed and then pulverized to form powdery dusts.

In order to demonstrate the excellent herbicidal effect of the present herbicidal compositions thus prepared, experiments are given below. There were also evaluated phytotoxicity of herbicidal compositions to rice plants.

EXPERIMENT 1

Herbicidal effects against barnyard grass and phytotoxicity to rice plants

Wagner pots, each having a surface area of 1/5,000 are, were packed with paddy field soil. In each pot were transplanted four rice seedlings (cultivar: Akihikari) at 2.0 leaf stage. 50 Seeds of barnyard grass (*Echinochloa crus-galli*) were incorporated into the soil. Then, each pot was flooded to about 1 cm in depth and kept under flooded conditions. When the barnyard grass grew up to 1.5 leaf-stage and 3.0 leaf-stage, a prescribed amount of emulsifiable concentrates prepared according to the procedures in Example 10, was dropwise applied into the paddy water by the use of a measuring pipet. After 25 days from the application of the emulsifiable concentrates, herbicidal effects on weeds and phytotoxicity to rice plants were evaluated.

Using comparative compositions containing active ingredients listed in Table 1, substantially the same procedures as described above were repeated to evaluate their herbicidal effects on weeds and phytotoxicity to rice plants. The results are shown in Table 1.

Herbicidal effects were evaluated based on five appraisal points which were assigned as follows.

| Evaluation of Herbicidal Activity Against Weeds | |
|---|---|
| Points | Percentage of destruction of weeds |
| 5 | more than 90% |
| 4 | 70 to 89% |
| 3 | 50 to 69% |
| 2 | 30 to 49% |
| 1 | 10 to 29% |
| 0 | less than 10% |

| Evaluation of Phytotoxicity to Rice Plants | |
|---|---|
| Points | Percentage of growth-inhibition of rice plants |
| 5 | more than 90% |
| 4 | 70 to 89% |
| 3 | 50 to 69% |
| 2 | 30 to 49% |
| 1 | 10 to 29% |
| 0 | less than 10% |

As is apparent from Table 1, with respect to all of the present compounds employed, there were achieved excellent herbicidal activities. With respect to the comparative compounds employed, Compound 10 and Compound 12 indicated sufficient herbicidal activities. The representative conventional herbicide "Molinate" (Compound 13) indicated a sufficient herbicidal activity to barnyard grass at 1.5 leaf-stage, but indicated a poor herbicidal activity to barnyard grass at 3.0 leaf-stage as compared with that of the compounds according to the present invention. Other comparative compounds indicated poor herbicidal activities as compared with the compounds of the present invention.

TABLE 1

| | | 1.5 leaf-stage of barnyard grass | | 3 leaf-stage of barnyard grass | |
|---|---|---|---|---|---|
| Compound | Dose [g/10a.] | herbicidal activity (barnyard grass) | phytotoxicity (rice plant) | herbicidal activity (barnyard grass) | phytotoxicity (rice plant) |
| PRESENT INVENTION | | | | | |
| Compound 1 | 600 | 5 | 1 | 5 | 0 |
| | 300 | 5 | 0 | 5 | 0 |
| | 150 | 5 | 0 | 5 | 0 |
| Compound 2 | 600 | 5 | 0 | 5 | 0 |
| | 300 | 5 | 0 | 5 | 0 |
| | 150 | 5 | 0 | 5 | 0 |
| Compound 3 | 600 | 5 | 1 | 5 | 0 |
| | 300 | 5 | 0 | 5 | 0 |
| | 150 | 5 | 0 | 4 | 0 |
| Compound 4 | 600 | 5 | 0 | 5 | 0 |
| | 300 | 5 | 0 | 5 | 0 |
| | 150 | 5 | 0 | 4 | 0 |
| Compound 5 | 600 | 5 | 0 | 5 | 0 |
| | 300 | 5 | 0 | 4 | 0 |
| | 150 | — | — | — | — |
| Compound 6 | 600 | 5 | 2 | 5 | 1 |
| | 300 | 5 | 0 | 5 | 0 |
| | 150 | 5 | 0 | 5 | 0 |
| Compound 7 | 600 | 5 | 0 | 5 | 0 |
| | 300 | 5 | 0 | 5 | 0 |
| | 150 | 5 | 0 | 5 | 0 |
| Compound 8 | 600 | 5 | 0 | 5 | 0 |
| | 300 | 5 | 0 | 5 | 0 |
| | 150 | 5 | 0 | 5 | 0 |
| COMPARATIVE (see note) | | | | | |
| Compound 10 | 600 | 5 | 0 | 5 | 0 |
| | 300 | 5 | 0 | 5 | 0 |
| | 150 | 5 | 0 | 5 | 0 |
| Compound 11 | 600 | 5 | 2 | 3 | 1 |
| | 300 | 4 | 0 | 3 | 0 |
| | 150 | 3 | 0 | 1 | 0 |
| Compound 12 | 600 | 5 | 0 | 5 | 0 |
| | 300 | 5 | 0 | 5 | 0 |
| | 150 | 5 | 0 | 5 | 0 |
| Compound 13 (Molinate) | 600 | 5 | 2 | 4 | 1 |
| | 300 | 5 | 0 | 3 | 0 |
| | 150 | 4 | 0 | 3 | 0 |
| Compound 14 | 300 | — | — | 3 | 0 |
| Compound 15 | 300 | — | — | 3 | 0 |
| Compound 16 | 300 | — | — | 3 | 0 |
| Compound | 300 | | | | |

TABLE 1-continued

| | | 1.5 leaf-stage of barnyard grass | | 3 leaf-stage of barnyard grass | |
|---|---|---|---|---|---|
| Compound | Dose [g/10a.] | herbicidal activity (barnyard grass) | phyto-toxicity (rice plant) | herbicidal activity (barnyard grass) | phyto-toxicity (rice plant) |
| Compound 17 pound 17 | | | | | |
| Compound 18 Com-pound 18 | 300 | — | — | 2 | 0 |
| Compound 19 Com-pound 19 | 300 | — | — | 1 | 0 |

TABLE 1-continued

| Compound | Dose [g/10a.] | 1.5 leaf-stage of barnyard grass herbicidal activity (barnyard grass) | phyto-toxicity (rice plant) | 3 leaf-stage of barnyard grass herbicidal activity (barnyard grass) | phyto-toxicity (rice plant) |
|---|---|---|---|---|---|
| None | — | 0 | 0 | 0 | 0 | note:
The comparative compounds employed are as follows.

Compound 10: $(C_2H_5)_2N-C(=O)-S(CH_2)_3Cl$

Compound 11: hexahydroazepine-N-C(=O)-S(CH$_2$)$_2$Cl (with 3-methyl)

Compound 12: hexahydroazepine-N-C(=O)-S(CH$_2$)$_3$Cl (with 3-methyl)

Compound 13 (Molinate): hexahydroazepine-N-C(=O)-S(CH$_2$)$_2$H (3-methyl)

Compound 14: 2,6-dimethylpiperidine-N-C(=O)-SCH$_3$

Compound 15: 2,6-dimethylpiperidine-N-C(=O)-S(CH$_2$)$_2$H

Compound 16: 2,6-dimethylpiperidine-N-C(=O)-S(CH$_2$)$_3$H

Compound 17: 2,6-dimethylpiperidine-N-C(=O)-S(CH$_2$)$_4$H

Compound 18: 2,6-dimethylpiperidine-N-C(=O)-S(CH$_2$)$_8$H

Compound 19: 2,6-dimethylpiperidine-N-C(=O)-S(CH$_2$)$_{10}$H

EXPERIMENT 2

Herbicidal effects against paddy field weeds and phytotoxicity to rice plants With respect to more broad spectrum of weeds, there were conducted experiments on herbicidal activity to weeds and phytotoxicity to rice plants of the compounds of the present invention and the comparative compounds (Compound 10, Compound 12 and Compound 13).

Wagner pots each having a surface area of 1/5000 (are) were packed with paddy field soil. In each pot were transplanted four rice seedlings (cultivar: Akihikari) at 2.0 leaf stage having a height of 10 cm. Soil containing a large number of seeds of barnyard grass and major paddy field weeds was incorporated into the surface soil of 1 to 2 cm in depth, and three tubers of "Mizugayatsuri" (*Cyperus serotinus*) were planted in the soil. The soil in each pot was kept under wet conditions for a week. Then, each pot was flooded to about 5 cm in depth and kept under flooded conditions. When the barnyard grass grew up to 2.5 leaf-stage, the granules prepared according to the procedures in Example 11 were applied into the paddy water. After 25 days from the treatment, the herbicidal effects and phytotoxicity to rice plants were evaluated. The results are shown in Table 2.

Using the comparative compounds listed in Table 2, substantially the same procedures as described above were repeated to observe herbicidal effects on paddy field weeds and phytotoxicity to rice plants. The results are also shown in Table 2.

The herbicidal effects and phytotoxicity were evaluated by the same as in Experiment 1.

As is apparent from Table 2, all of the compounds of the present invention and the comparative compounds (Compound 10, and Compound 12) indicated excellent herbicidal activities without harmful effects to rice plants as compared with that of the representative conventional herbicide "Molinate" (Compound 13).

TABLE 2

| Compound | Dose [g/10a.] | Herbicidal activity | | | | phytotoxicity rice plant |
|---|---|---|---|---|---|---|
| | | barnyard grass | broad-leaf weeds | Hotarui (*Scirpus juncoides*) | Mizugayatsuri (*Cyperus serotinus*) | |
| PRESENT INVENTION | | | | | | |
| Compound 1 | 600 | 5 | 5 | 5 | 5 | 0 |
| | 300 | 5 | 5 | 5 | 4 | 0 |
| | 150 | 5 | 5 | 4 | 4 | 0 |
| Compound 2 | 600 | 5 | 5 | 5 | 5 | 0 |
| | 300 | 5 | 5 | 4 | 4 | 0 |
| | 150 | 5 | 5 | 3 | 3 | 0 |
| Compound 3 | 600 | 5 | 5 | 5 | 5 | 0 |
| | 300 | 5 | 5 | 4 | 4 | 0 |
| | 150 | 5 | 4 | 3 | 4 | 0 |
| Compound 4 | 600 | 5 | 5 | 5 | 5 | 0 |
| | 300 | 5 | 4 | 4 | 3 | 0 |
| | 150 | 4 | 3 | 2 | 2 | 0 |
| Compound 5 | 600 | 5 | 5 | 5 | 5 | 0 |
| | 300 | 5 | 4 | 4 | 3 | 0 |
| | 150 | — | — | — | — | — |
| Compound 6 | 600 | 5 | 5 | 5 | 5 | 1 |
| | 300 | 5 | 5 | 5 | 4 | 0 |
| | 150 | 5 | 4 | 4 | 3 | 0 |
| Compound 7 | 600 | 5 | 5 | 5 | 5 | 0 |
| | 300 | 5 | 5 | 5 | 4 | 0 |
| | 150 | 5 | 4 | 3 | 3 | 0 |
| Compound 8 | 300 | 5 | 5 | 5 | 4 | 0 |
| | 150 | 5 | 3 | 3 | 2 | 0 |

TABLE 2-continued

| Compound | Dose [g/10a.] | Herbicidal activity | | | | phytotoxicity rice plant |
|---|---|---|---|---|---|---|
| | | barnyard grass | broad-leaf weeds | Hotarui (*Scirpus juncoides*) | Mizugayatsuri (*Cyperus serotinus*) | |
| COMPARATIVE | | | | | | |
| Compound 10 | 600 | 5 | 5 | 5 | 5 | 0 |
| | 300 | 5 | 5 | 4 | 4 | 0 |
| | 150 | 5 | 5 | 4 | 4 | 0 |
| Compound 12 | 600 | 5 | 5 | 5 | 5 | 0 |
| | 300 | 5 | 5 | 5 | 4 | 0 |
| | 150 | 5 | 5 | 4 | 4 | 0 |
| Compound 13 | 600 | 5 | 3 | 2 | 1 | 2 |
| | 300 | 4 | 2 | 1 | 1 | 0 |
| | 150 | 3 | 1 | 0 | 0 | 0 |
| None | — | 0 | 0 | 0 | 0 | 0 |

EXPERIMENT 3

Acute toxicity to fish

With respect to the compounds according to the present invention and the comparative compounds (Compound 10, Compound 12 and Compound 13), there were conducted tests on acute toxicity to carps.

In 25-liter water tanks made of glass was charged 20 liters of water. 12 Black-carp fry were released to each of the water tanks and bred while feeding for 7 days. Then, the whole quantity of water in each of the tanks was replaced with fresh water, and feeding to the carps was stopped. After three days, a prescribed amount of 1 weight % solution of a test compound in acetone was added to water in the water tank.

The number of survival fish in each tank was counted after 24 hours, 48 hours and 96 hours, successively.

The TLm (median tolerance limit=lethal concentration 50%) was determined by the Doudorff's method (Sewage & Ind. Wastes 23 (1951) 1380–1397).

The results are shown in Table 3.

As is apparent from Table 3, the TLm's (48 hours) were more than 1 ppm with respect to the compounds according to the present invention and the comparative compounds except Compound 12.

TABLE 3

| Compound | Median lethal concentration (ppm) | | |
|---|---|---|---|
| | TLm (24hrs) | TLm (48hrs) | TLm (96hrs) |
| PRESENT INVENTION | | | |
| Compound 1 | — | 11 | 10 |
| Compound 6 | — | 4.4 | 3.7 |
| Compound 7 | — | 2.6 | 2.6 |
| COMPARATIVE | | | |
| Compound 10 | — | >20 | 18 |
| Compound 12 | 1.0 | <0.5 | — |
| Compound 13 | — | 34 | — |

EXPERIMENT 4

Subacute toxicity to fish

With respect to the compounds according to the present invention and the comparative compounds listed in Table 4, there were conducted tests on subacute toxicity to 2-year-old carps having an average weight of 20 g.

Ten 2-year-old carps were released in each of 25-liter water tanks equipped with an air-blowing apparatus and acclimatized to the surroundings while feeding for 10 days. Water in each of the water tanks was continuously replaced with fresh water so that the residence time of water in the water tanks is 6 hours. Each test compound was added to a predetermined quantity of supply water to prepare a 0.2 ppm aqueous solution of each compound, and each of the aqueous solutions was continuously added to the water in the tank. After three weeks, the hematocrit values of all the survival carps were determined. The hematocrit value used herein is intended to mean a volume percentage of erythrocyte contained in the blood. The results are shown in Table 4.

As is apparent from Table 4, when the compounds according to the present invention were added to the water in the tank, the carps in the water tank did not develop any symptoms of anemia. Further, the compounds according to the present invention showed substantially no subacute toxicity to carps, so that all the carps survived. On the other hand, when the comparative compounds (Compound 10, Compound 12 and Compound 13) having high herbicidal activities were added to the water in the water tank, carps developed remarkable symptons of anemia. Further, the comparative compounds showed a high subacute toxicity to carps, so that the survival rate of carps was extremely low as compared with that of carps in the case where the compounds according to the present invention were added to the water in the tank.

Therefore, if the compositions containing such comparative compounds as active ingredients are applied into the hydrosphere such as paddy field, there is a high possibility that they give harmful effects against organisms which live in the hydrosphere.

TABLE 4

| Compound | Survival rate after 3 weeks (%) | Average Hematocrit Value (%) of survival fish |
|---|---|---|
| PRESENT INVENTION | | |
| Compound 1 | 100 | 30 |
| Compound 2 | 100 | 30 |
| Compound 6 | 100 | 34 |
| Compound 7 | 100 | 34 |
| Compound 8 | 100 | 35 |
| COMPARATIVE | | |
| Compound 10 | 80 | 16 |
| Compound 12 | 70 | 19 |
| Compound 13 | 50 | 25 |
| None | 100 | 35 |

What is claimed is:

1. A compound represented by the formula

wherein Z represents

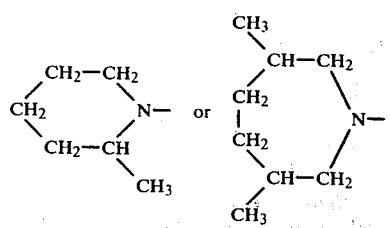

and when Z is

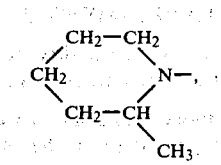

n is an integer of 4 to 10, whereas when Z is

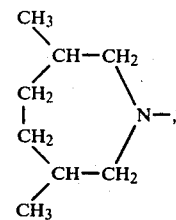

n is an integer of 3 to 10.

2. S-(4-chlorobutyl)-3,6-dimethyl-hexahydro-1H-azepine-1-carbothioate.

3. S-(3-chloropropyl)-3,6-dimethyl-hexahydro-1H-azepine-1-carbothioate.

4. S-(4-chlorobutyl)-(2-methyl)-piperidine-1-carbothioate.

5. A herbicidal composition which comprises as an active ingredient a herbicidally effective amount of a compound represented by the formula

wherein Z represents

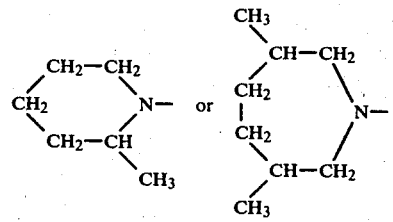

and when Z is

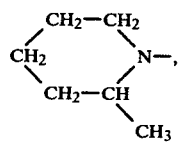

n is an integer of 4 to 10, whereas when Z is

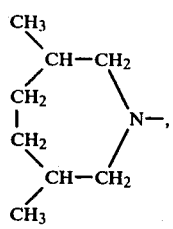

n is an integer of 3 to 10 and an agriculturally acceptable carrier.

6. A herbicidal composition according to claim 5, wherein said compound is selected from the group consisting of
S-(4-chlorobutyl)-3,6-dimethyl-hexahydro-1H-azepine-1-carbothioate,
S-(3-chloropropyl)-3,6-dimethyl-hexahydro-1H-azepine-1-carbothioate and
S-(4-chlorobutyl)-(2-methyl)-piperidine-1-carbothioate.

7. A herbicidal composition according to claim 5, wherein said compound is contained in an amount of 0.1 to 99% by weight based on the composition.

8. A method for the destruction of undesirable weeds which comprises applying to said weeds a herbicidal amount of a compound represented by the formula

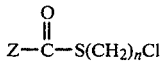

wherein Z represents

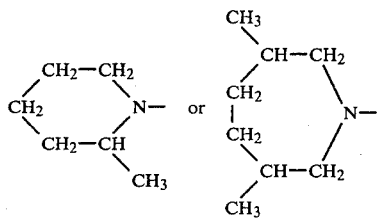

and when Z is

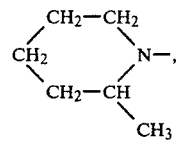

n is an integer of 4 to 10, whereas when Z is

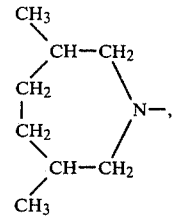

n is an integer of 3 to 10.

9. A method according to claim 8, wherein said compound is selected from the group consisting of
S-(4-chlorobutyl)-3,6-dimethyl-hexahydro-1H-azepine-1-carbothioate,
S-(3-chloropropyl)-3,6-dimethyl-hexahydro-1H-azepine-1-carbothioate and
S-(4-chlorobutyl)-(2-methyl)-piperidine-1-carbothioate.

10. A method according to claim 8, wherein said herbicidal amount is within the range of 10 g to 1000 g of said compound per 10 ares.

* * * * *